US010667864B2

(12) United States Patent
Feilkas et al.

(10) Patent No.: US 10,667,864 B2
(45) Date of Patent: Jun. 2, 2020

(54) INLINE-VIEW DETERMINATION

(71) Applicant: Brainlab AG, Munich (DE)

(72) Inventors: Thomas Feilkas, Kirchseeon (DE);
Thomas Drexl, Poing (DE); Sabrina Sainer, Munich (DE); Jorge Acosta, Munich (DE); Martin Lohmann, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 15/781,982

(22) PCT Filed: Apr. 19, 2017

(86) PCT No.: PCT/EP2017/059284
§ 371 (c)(1),
(2) Date: Jun. 6, 2018

(87) PCT Pub. No.: WO2018/192649
PCT Pub. Date: Oct. 25, 2018

(65) Prior Publication Data
US 2020/0100841 A1 Apr. 2, 2020

(51) Int. Cl.
*G06K 9/00* (2006.01)
*A61B 34/10* (2016.01)
(Continued)

(52) U.S. Cl.
CPC ........ *A61B 34/10* (2016.02); *A61B 17/00234* (2013.01); *A61B 2034/107* (2016.02);
(Continued)

(58) Field of Classification Search
None
See application file for complete search history.

(56) References Cited

U.S. PATENT DOCUMENTS

2008/0009697 A1   1/2008   Haider et al.
2014/0135616 A1   5/2014   Stein et al.

FOREIGN PATENT DOCUMENTS

WO   2010058398 A2   5/2010
WO   2016059256 A1   4/2016

OTHER PUBLICATIONS

International Search Report and Written Opinion issued in International Patent Application No. PCT/EP2017/059284 dated Jan. 9, 2018.

*Primary Examiner* — Atiba O Fitzpatrick
(74) *Attorney, Agent, or Firm* — Middleton Reutlinger

(57) ABSTRACT

The present invention relates to a computer-implemented medical data processing method for determining a 2D-view within an acquired 3D-image-dataset of a patient, wherein the method comprises executing, on a processor of a computer, the following steps: a) a representation of at least one anatomical structure (2) of interest is identified in the 3D-image-dataset and registered with the at least one anatomical structure (2); b) the spatial position of the at least one anatomical structure (2) and the spatial position of a predetermined section of a medical instrument (1) are determined in real space; c) the 2D-view is determined within the 3D-image-dataset, wherein the view-plane of the 2D-view is defined on the basis of the spatial position of the medical instrument (1), and wherein the view-center (B) of the 2D-view is defined on the basis of the relative spatial position of a predetermined section of the medical instrument (1) and the at least one anatomical structure (2); d) the relative position of the defined view-center with respect to a predetermined section of the medical instrument (1) is maintained in the 2D-view. The present invention further relates to a corresponding computer program, a corresponding program storage medium and a corresponding system for performing such method.

15 Claims, 5 Drawing Sheets

(51) Int. Cl.
  *A61B 34/00* (2016.01)
  *A61B 34/20* (2016.01)
  *A61B 90/00* (2016.01)
  *A61B 17/00* (2006.01)
(52) U.S. Cl.
  CPC . *A61B 2034/2065* (2016.02); *A61B 2034/256* (2016.02); *A61B 2090/374* (2016.02); *A61B 2090/3762* (2016.02)

INLINE-VIEW DETERMINATION

TECHNICAL FIELD

The present invention relates to a computer implemented method for determining a 2D-view within an acquired 3D-image-dataset of a patient, and to a corresponding computer program and system.

SUMMARY

In medical procedures involving image guided surgery (IGS), for example spinal navigation, it is desirable to display reconstructions (arbitrarily oriented 2D slices that are not the original slices/images created by the scanner) that enable the surgeon to see the most relevant anatomy/information and automatically configure the system according to the approach.

The present invention addresses these persisting desires and provides automated, optimized and situation/anatomy-specific views for a medical procedure, particularly for a spinal navigation application, involving image data that may have been acquired by a medical imaging device such as CT, MR, cone beam CT and the like. Consequently, the need for manual interaction is significantly reduced compared to prior art image guided surgery. The present invention may include one or more of the following features:

"Inline Views": For navigation purpose inline views are better suited than simple axial/coronal/sagittal (ACS) views. Spine software has been using inline views related not only to the instrument, but also to the data set (e.g. plane of LR-axis and instrument axis). Thereby the inline views have always been centered on the instrument tip. The invention provides inline views centered on the relevant anatomy structure instead of the instrument tip. Consequently, a better focus on the region of interest (e.g. trajectory) is acquired for minimal invasive surgery (MIS), including more stable views that are moving less than before.

"Anatomy detection": To center the inline views on the anatomy, the location of the spinal column has to be known. Therefore an algorithm capable to detect or segment the Spinal column is needed. While an algorithm to approximate the location of the spine may be utilized for this purpose, utilizing an anatomical atlas is also conceivable.

"View Center and Direction": From anatomy detection a view center shall be calculated, so that, for example, the vertebrae are centered. For inline plane calculation, also derive the local vertebra AP/HF/LR directions (vertebras in scoliosis can have completely different local directions than the patient orientations).

"Initial View Orientation": The initial view orientation can be automatically setup based on DICOM data if available, based on disease classification, and even on the IR-camera position and orientation in relation to a registration with respect to a reference array.

"Inline View Switching": Depending on the approach direction, the view calculations shall switch automatically to always present a proper view direction. There may be a hysteresis to avoid switching forth and back, e.g. switch forth at 60° and back at 30°.

"Automatic Zoom": Provide specific zoom level for specific surgical step (e.g. if a drillguide is on the pedicle, then zoom in) or depending on the instrument location in regard to the anatomy.

"View Selection": Provide specific views for specific surgical step or depending on the instrument location in regard to the anatomy (e.g. if a drillguide is on the pedicle, then show a Probe's Eye view).

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:

the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

A pointer is a rod which comprises one or more—advantageously, two—markers fastened to it and which can be used to measure individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand. Determining the position is referred to as referencing if it implies informing a navigation system of said position in a reference system of the navigation system.

Preferably, atlas data is acquired which describes (for example defines, more particularly represents and/or is) a general three-dimensional shape of the anatomical body part. The atlas data therefore represents an anatomical atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

Within spinal navigation (e.g. Brainlab Spine & Trauma 3D Navigation Software) it is important to display reconstructions (arbitrarily oriented 2D slices that are not the original slices/images created by the scanner) that enable the surgeon to see the most relevant part of the anatomy with regards to the navigated instrument and to display it such, that it is intuitive to understand with regards to the surgical approach and the setup. This is needed to e.g. find a trajectory for an implant. Purpose of the invention is to offer reconstructions, which are automated, optimized, situation and anatomy-specific for a spinal navigation application with image data (CT, MR, cone beam CT). Therewith the user shall be supported in regards to automation, intuitivity and usability of the software (less manual interaction, optimal views).

BRIEF DESCRIPTION OF DRAWINGS

In the following, the invention is described with reference to the enclosed figures which represent preferred embodiments of the invention. The scope of the invention is however not limited to the specific features disclosed in the figures, which show.

DETAILED DESCRIPTION

Figure 1:
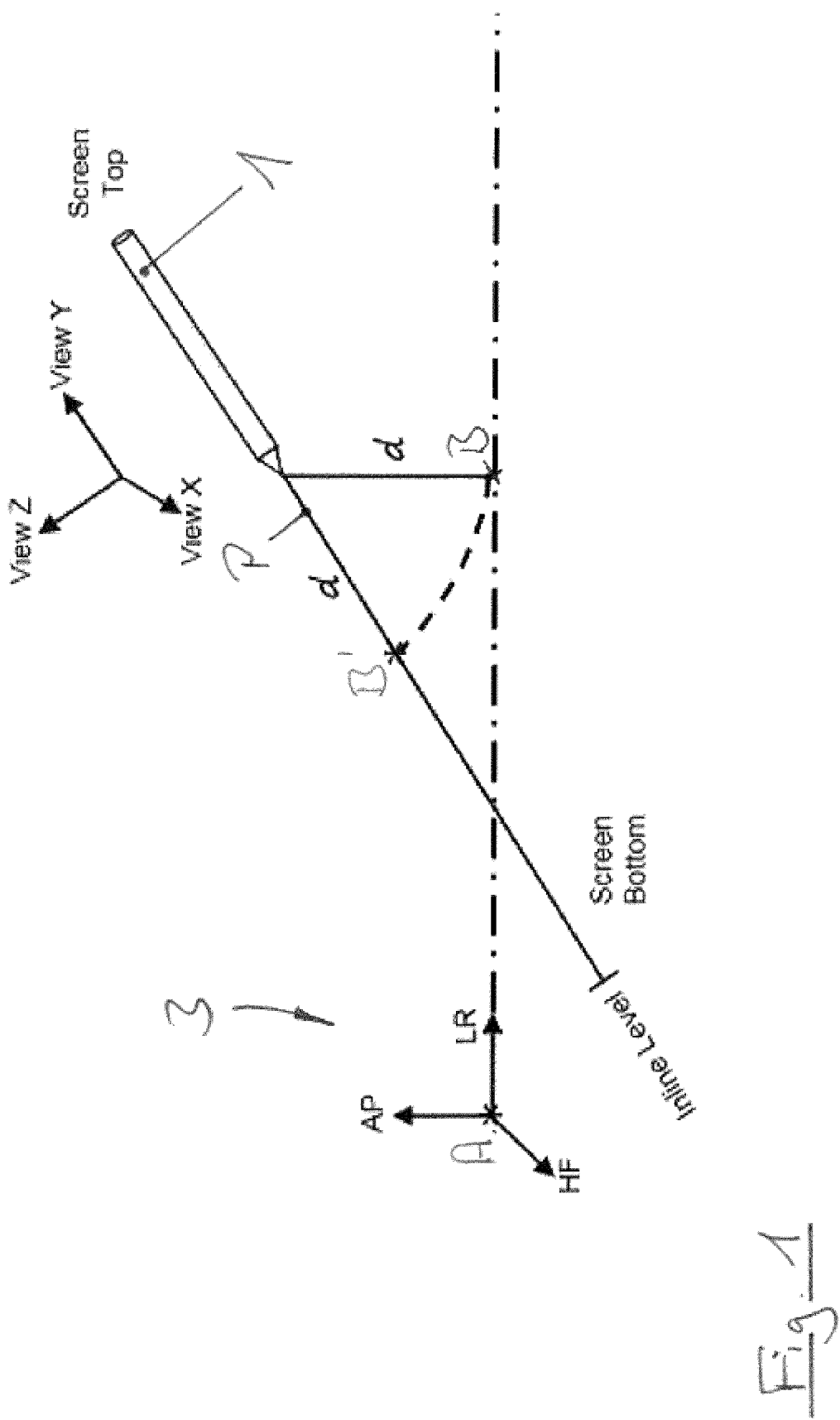
FIGS. 1/2 schematically show a possible setup in accordance with the inventive method.

Inline Views:

In accordance with the present invention, a relative position of a defined view center with respect to a predefined part of the instrument (e.g. the tip) can, for example, be maintained in a 2D view in a manner as described in the following:

The view is centered on the detected bone anatomy 2, rather than on the position, of the instrument 1 so all vertebras 2 are automatically centered on the screen 4 even while the surgeon is working on skin level. The instrument's tip position on the screen 4 is independent from the instrument's orientation: changing the instrument's orientation while leaving the tip in the same position will hold the tip fixed on the screen 4 although the inline planes are changing. This allows e.g. to find the trajectory direction P when the tip is on the trajectory entry point.

In order to fix the view center B of the inline views to the anatomy 2, it is not sufficient to simply shift the plane: The instrument's 1 position on the screen 4 depends on the view's orientation. Even if the instrument tip is held at a fixed location, the tip is shown at varying positions in the view when the instrument 1 is rotated, because the intersection of instrument axis P and view center plane has a varying distance d towards the tip. Therefore, if the tip shall be displayed at a fixed location in the view while the instrument 1 is rotated around the tip, the view center B has to be shifted on the fly. The intention to shift the instrument tip only in one view axis (y-axis) comes due to the reason that the approach direction shall display the vertebra 2 (region of interest), not the region around the instrument 1 while the approaches perpendicular direction can be centered to the instrument 1.

Figure 2:
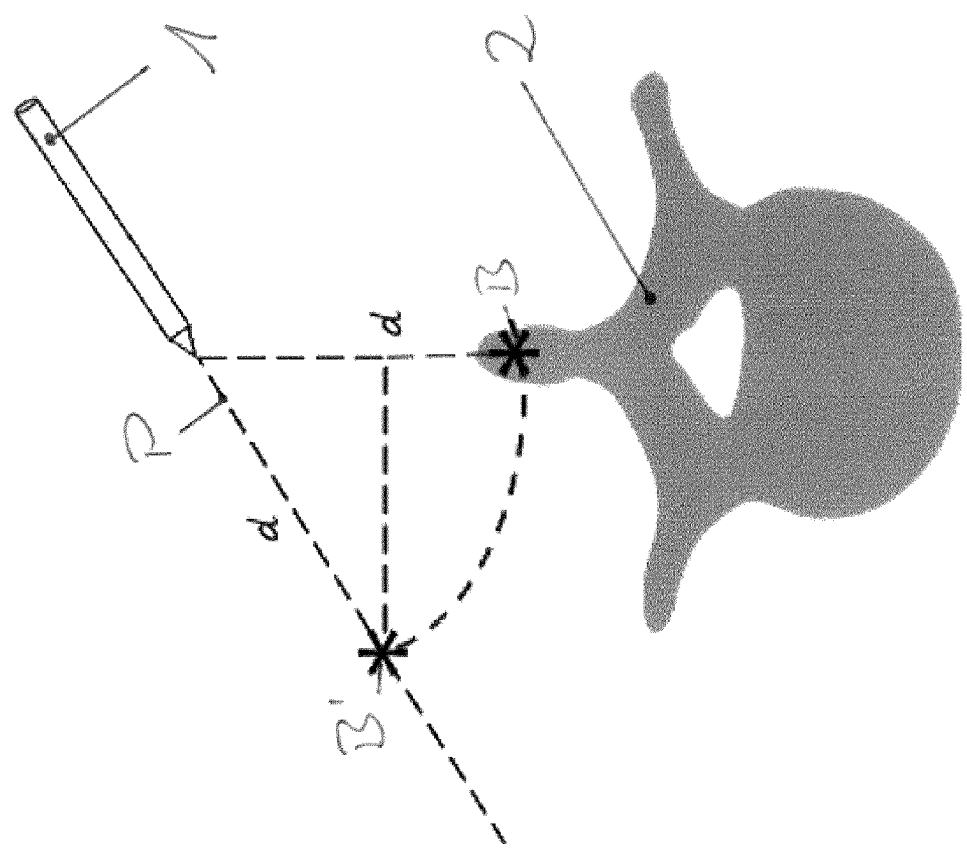
Figure 3:
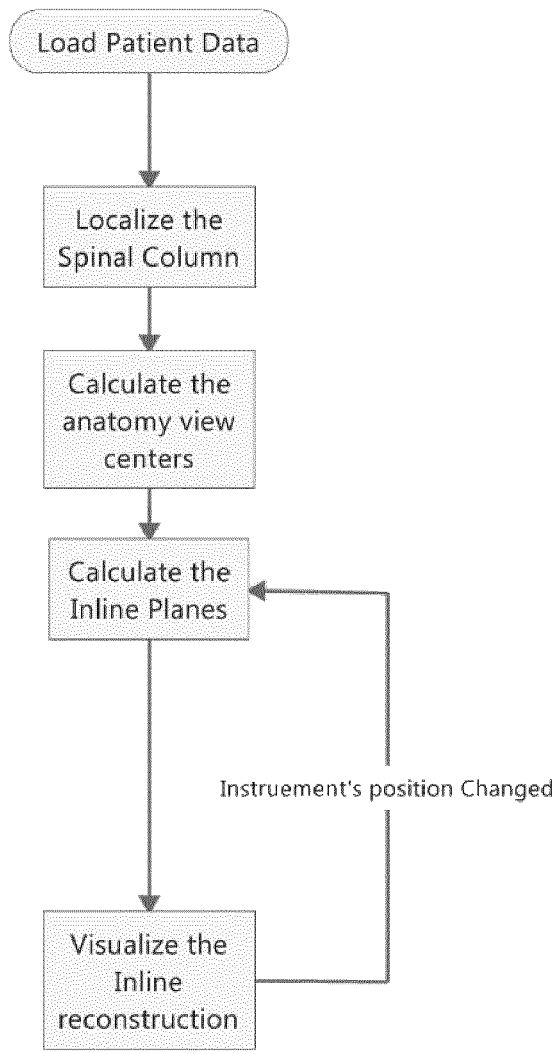
FIG. 3 shows a possible approach for performing the inventive method.

The view center B is calculated by projecting the instrument tip onto a plane of the patient/vertebra coordinate system 3 that is implicitly used for centering (see origin A in FIG. 1, the tip is projected to the LR-HF plane) to get the distance d of the tip to the view center B. This distance d is then used to find the view center B on the instrument axis P. However, this view center B is not yet correct, because the instrument 1 is not fixed to the view's y-axis (see FIG. 1, the instrument 1 can approach from the side of the view like the view's x-axis). Therefore, the view center B has to be projected again onto the proper plane through the instrument 1 (see Point B' in FIGS. 1 and 2), so the instrument tip gets a fixed location in the view.

View Center:

Possible sources to determine the view center B include at least one of the following:
1. an algorithm to approximate the location and curvature (particularly only AP) of the spinal column within a 3D Dataset.
2. a segmentation of the vertebras acquired from an anatomical atlas.

Figure 4:
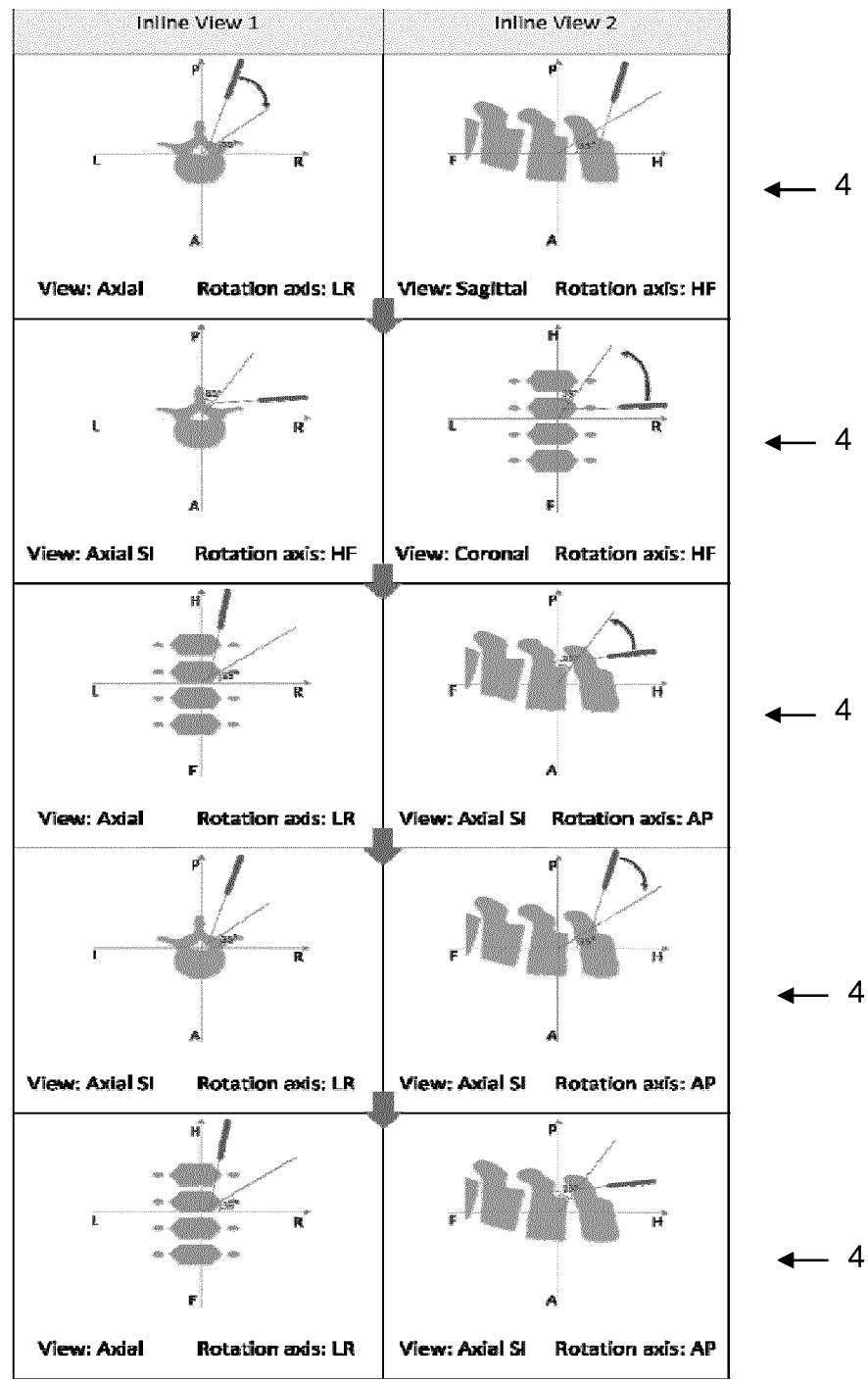
FIG. 4 shows a display modality in accordance with the present invention.

Inline View Switching:

The spinal fusion workflow normally requires simply an Axial Inline (LR fixed) and a Sagittal Inline view (HF fixed). However, in general, all patient directions can be either fixed to the x-axis or y-axis of the view. Depending on the approach direction, the view calculations may switch automatically to always present a proper view direction. There may be a hysteresis to avoid switching forth and back, therefore the view shall switch forth at 60 degree and back at 30 degree. The images in FIG. 4 show the intended behavior of the automatic switching.

Moreover, the view selection may change the view orientation for showing the instrument 1 on Top, Left, or Right of the view and never approaching from the bottom so as to obtain an optimal view.

Anatomy Detection:

An algorithm finds a curve through the processes of the vertebras 2 searching for symmetry and for bone that looks like a (short) vertebra process, and/or An algorithm finds a curve along the anterior points of the vertebra 2 bodies using the curve through processes and searching for the anterior point in anterior direction by applying (pre-created) pattern matchings (like "one-dimensional atlases" of the vertebra); or An anatomical atlas may build a local relationship between the atlas and every useful anatomical data set of the patient. The result is a deformable registration, which connects every pixel of the image data set with a position in the atlas. By means of this registration the atlas delivers different information e.g. region of interest, organ segmentation and body part detection, enhancing the reliability of the vertebras' location and orientation.

Figure 5:
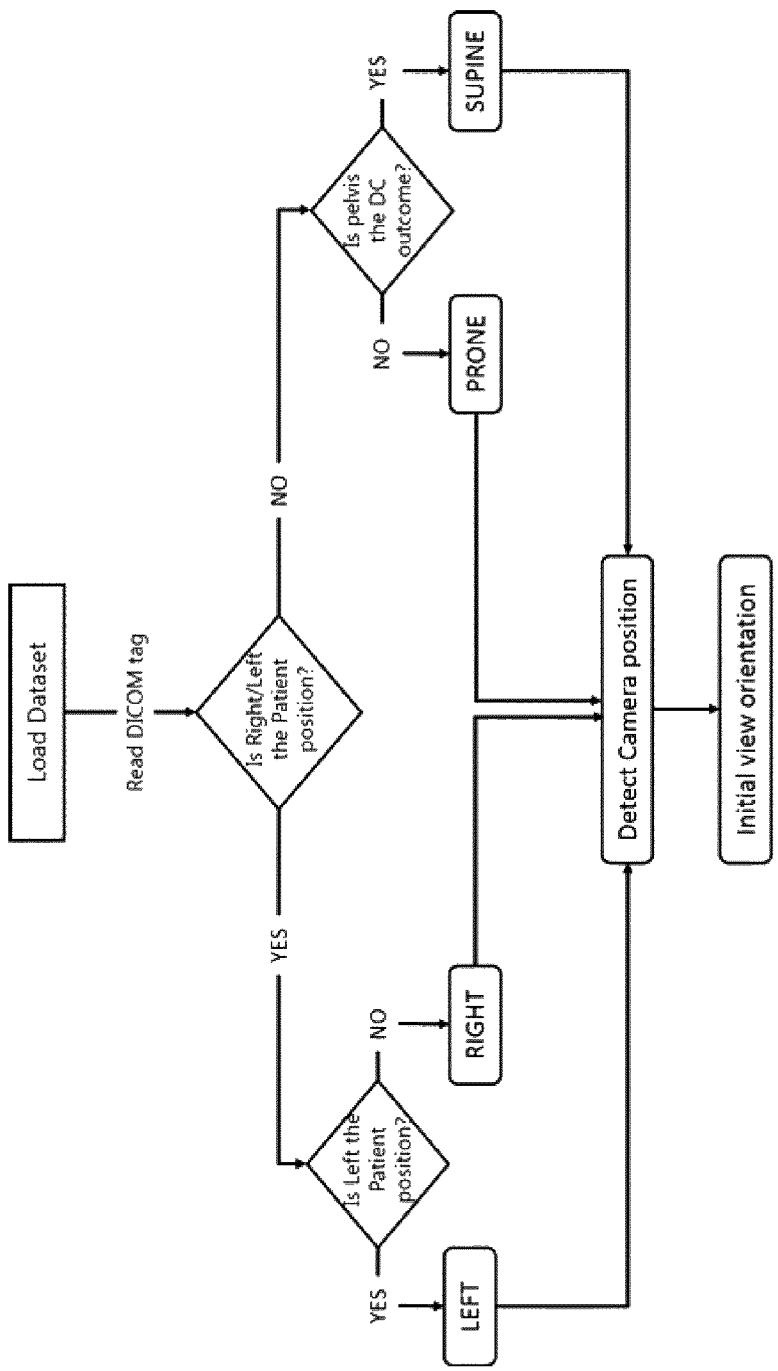
FIG. 5 shows an approach for defining an initial view orientation in accordance with the present invention.

Initial View Orientation:

The initial view orientation is automatically setup without user interaction and defines the initial orientation of the patient with respect to the screen coordinate system. The invention may automatize (please refer to FIG. 5) the process of initializing the view orientation that matches with the OR-setup, including the position of the tracking camera array of the navigation system and the relative position of the patient, the screen/display and the surgeon, by combining the inputs of the surgery workflow, which then lead to less interaction with the screen/display and reduce the steps for starting the navigation. The initial view orientation may be derived from:
1. Patient Position/Orientation in DICOM data set.
2. Disease Classification
3. IR-Camera position, registration, reference array (patient location).

Automatic Zoom:

Specific field of view levels for specific surgical steps (e.g. if drillguide is on the pedicle, then zoom in, with the vertebra being still depicted at the view center) or depending on the instrument location in regards to the anatomy 2 are provided.

The invention claimed is:

1. A computer-implemented method for determining a 2D-view within an acquired 3D-image-dataset of a patient, wherein the method comprises executing, on a processor of a computer, the following steps:
   identifying a representation of at least one anatomical structure in the 3D-image-dataset and registering the representation with the at least one anatomical structure;
   determining the spatial position of the at least one anatomical structure and the spatial position of a predetermined section, particularly a tip of a medical instrument in real space;
   determining the 2D-view within the 3D-image-dataset, wherein the view-plane of the 2D-view is defined on the basis of the spatial position of the medical instrument, and wherein the view-centre of the 2D-view is defined on the basis of the relative spatial position of the predetermined section of the medical instrument and the at least one anatomical structure;
   maintaining the relative position of the defined view-centre with respect to the predetermined section of the medical instrument in the 2D-view when the spatial orientation of the medical instrument is changed.

2. The method according to claim 1, wherein determining the 2D-view includes defining at least one co-ordinate system for the at least one anatomical structure (2), particularly at least one separate co-ordinate system for each anatomical structure, wherein the at least one co-ordinate system is defined by an origin, an anterior-posterior-axis, a left-right-axis and a head-feet-axis being specific to the anatomical structure.

3. The method according to claim 2, wherein defining at least one separate co-ordinate system for each of a plurality of anatomical structures includes interpolating between the co-ordinate systems defined for different anatomical structures.

4. The method according to claim 1, wherein determining the 2D-view includes aligning, particularly at a predefined, specifically manually defined distance, the view-center of the 2D-view with a defined reference of the anatomical structure, the reference being represented by one of:
   the origin of one of said co-ordinate systems defined for the anatomical structures;
   the center between opposing edges of the representation of the anatomical structure in the 2D-view;
   the center of area of the representation of the anatomical structure in the 2D-view.

5. The method according to claim 1, wherein an anatomical atlas is utilized for at least one of:
   registering the at least one anatomical structure with the 3D-dataset;
   defining the at least one co-ordinate system; and
   defining the reference.

6. The method according to claim 1, wherein the view-plane of the 2D-view includes:
   a pointing axis of the medical instrument, and
   an anterior-posterior-axis, a left-right-axis or a head-feet-axis defined for either the patient or for the anatomical structure.

7. The method according to claim 6, wherein it depends on the relative spatial position of the pointing axis of the medical instrument with respect to the anterior-posterior-axis, the left-right-axis and the head-feet-axis, whether the view-plane of the 2D-view includes the anterior-posterior-axis, the left-right-axis or the head-feet-axis, particularly wherein the view-plane including one of the anterior-posterior-axis, the left-right-axis and the head-feet-axis is changed to include one other of the anterior-posterior-axis, the left-right-axis and the head-feet-axis, as the pointing axis of the medical instrument is tilted over a predetermined threshold.

8. The method according to claim 1, wherein the anatomical structure is a bone structure, particularly a sacrum, a pelvis or a vertebra.

9. The method according to claim 1, wherein the 2D-view is determined for, and particularly interpolated between a plurality of anatomical structures, specifically wherein the current 2D-view is determined for the anatomical structure which is closest to the predetermined section of the medical instrument.

10. The method according to claim 1, wherein the 2D-view is displayed to the user on a display.

11. The method according to claim 1, wherein determining the 2D-view involves acquiring data as to the spatial OR-setup, particularly including at least one of:
   a patient position in real space;
   a patient orientation in a DICOM-type 3D-image-dataset;
   a disease-classification;
   IR-camera position in real space with respect to the display displaying the 2D-view, and/or the patient.

12. The method according to claim 1, wherein determining the 2D-view involves initializing and/or adapting a field of view of the 2D-view, particularly on the basis of the relative spatial position of the predetermined section of the medical instrument and the at least one anatomical structure.

13. The method according to claim 10, wherein the orientation of a representation of the medical instrument as shown on the display corresponds with the orientation of the medical instrument in real space, particularly wherein the instrument orientation is substantially consistent in a plurality of 2D-views shown on the display.

14. A non-transitory computer readable storage medium comprising a computer program stored on a memory operably connected to the computer and executed by at least one processor, which, when running on the computer, causes the computer to:
   identify a representation of at least one anatomical structure in the 3D-image-dataset and registering the representation with the at least one anatomical structure;
   determine the spatial position of the at least one anatomical structure and the spatial position of a predetermined section, particularly a tip of a medical instrument in real space;
   determine the 2D-view within the 3D-image-dataset, wherein the view-plane of the 2D-view is defined on the basis of the spatial position of the medical instrument, and wherein the view-centre of the 2D-view is defined on the basis of the relative spatial position of the predetermined section of the medical instrument and the at least one anatomical structure;
   maintain the relative position of the defined view-centre with respect to the predetermined section of the medical instrument in the 2D-view when the spatial orientation of the medical instrument is changed.

15. A system for determining a 2D-view within an acquired 3D-image-dataset of a patient, including a computer with associated memory on which a program is stored, the computer having at least one processor executing the program, the program having instructions to cause the computer to:
   identify a representation of at least one anatomical structure in the 3D-image-dataset and registering the representation with the at least one anatomical structure;
   determine the spatial position of the at least one anatomical structure and the spatial position of a predetermined section, particularly a tip of a medical instrument in real space;
   determine the 2D-view within the 3D-image-dataset, wherein the view-plane of the 2D-view is defined on the basis of the spatial position of the medical instrument, and wherein the view-centre of the 2D-view is defined on the basis of the relative spatial position of the predetermined section of the medical instrument and the at least one anatomical structure;
   maintain the relative position of the defined view-centre with respect to the predetermined section of the medical instrument in the 2D-view when the spatial orientation of the medical instrument is changed.

* * * * *